US012758699B2

(12) United States Patent
Locke

(10) Patent No.: US 12,758,699 B2
(45) Date of Patent: Oct. 13, 2026

(54) ABDOMINAL NEGATIVE-PRESSURE THERAPY DRESSING WITH CLOSED-LOOP FORCE MANAGEMENT CONTROL

(71) Applicant: Solventum Intellectual Properties Company, Maplewood, MN (US)

(72) Inventor: Christopher Brian Locke, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 15 days.

(21) Appl. No.: 17/619,931

(22) PCT Filed: Apr. 29, 2020

(86) PCT No.: PCT/US2020/030528
§ 371 (c)(1),
(2) Date: Dec. 16, 2021

(87) PCT Pub. No.: WO2020/256837
PCT Pub. Date: Dec. 24, 2020

(65) Prior Publication Data

US 2022/0305192 A1 Sep. 29, 2022

Related U.S. Application Data

(60) Provisional application No. 62/862,417, filed on Jun. 17, 2019.

(51) Int. Cl.
*A61M 1/00* (2006.01)

(52) U.S. Cl.
CPC ............ *A61M 1/916* (2021.05); *A61M 1/966* (2021.05); *A61M 1/915* (2021.05);
(Continued)

(58) Field of Classification Search
CPC ...... A61M 1/916; A61M 1/966; A61M 1/915; A61M 2205/0227; A61M 2205/3344;
(Continued)

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Philip R Wiest
*Assistant Examiner* — Eric Rassavong

(57) ABSTRACT

A dressing for treating an open abdominal cavity with negative pressure. In some embodiment, the dressing may comprise a viscera contact layer capable of communicating a negative pressure to the viscera and capable of forming flow paths for a fluid through the contact layer; a fluid manifold capable of being disposed adjacent to the contact layer and capable of communicating a negative pressure to a tissue and capable of forming flow paths for a fluid; and a sensor capable of acquiring data associated with strain in one or more of the fluid manifold and the viscera contact layer.

16 Claims, 7 Drawing Sheets

(52) U.S. Cl.
CPC ............... *A61M 2205/0227* (2013.01); *A61M 2205/3344* (2013.01); *A61M 2210/1021* (2013.01)

(58) Field of Classification Search
CPC ............. A61M 2210/1021; A61B 5/68; A61B 5/02427; A61B 2220/83; A47G 2200/066; A61F 2013/00957; A61F 13/05
See application file for complete search history.

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,764,732 | B2 * | 7/2014 | Hartwell ............. A61F 13/0209 604/319 |
| 8,834,451 | B2 | 9/2014 | Blott et al. |
| 8,926,592 | B2 * | 1/2015 | Blott ................... A61M 3/0229 604/9 |
| 9,017,302 | B2 * | 4/2015 | Vitaris .................. A61M 27/00 604/304 |
| 9,198,801 | B2 | 12/2015 | Weston |
| 9,211,365 | B2 | 12/2015 | Weston |
| 9,289,542 | B2 | 3/2016 | Blott et al. |
| 10,070,994 | B2 * | 9/2018 | Dodd ................ A61F 13/00068 |
| 10,124,098 | B2 * | 11/2018 | Dunn ................ A61F 13/00029 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2008/0245985 | A1 * | 10/2008 | Heim .................. F16K 99/0028 251/129.06 |
| 2010/0106184 | A1 * | 4/2010 | Coward ............ A61F 13/00025 606/213 |
| 2010/0121286 | A1 * | 5/2010 | Locke .................. A61B 17/085 602/53 |
| 2011/0054283 | A1 * | 3/2011 | Shuler .................... A61B 5/445 604/319 |
| 2011/0224630 | A1 * | 9/2011 | Simmons ................ A61F 13/05 604/317 |
| 2011/0224631 | A1 * | 9/2011 | Simmons .......... A61F 13/00995 604/319 |
| 2012/0136326 | A1 * | 5/2012 | Croizat ................. A61F 13/148 604/319 |
| 2012/0283674 | A1 | 11/2012 | Stevenson et al. |
| 2014/0005618 | A1 | 1/2014 | Locke et al. |

(56) References Cited

U.S. PATENT DOCUMENTS

| | | | | |
|---|---|---|---|---|
| 2014/0163491 | A1 | 6/2014 | Schuessler et al. | |
| 2014/0180225 | A1* | 6/2014 | Dunn | A61M 1/915 604/319 |
| 2014/0249495 | A1* | 9/2014 | Mumby | A61F 13/0223 604/385.01 |
| 2015/0080788 | A1 | 3/2015 | Blott et al. | |
| 2015/0094673 | A1* | 4/2015 | Pratt | A61M 1/74 604/318 |
| 2018/0353339 | A1* | 12/2018 | Locke | A61F 13/0223 |
| 2018/0353344 | A1* | 12/2018 | Locke | A61F 13/00995 |
| 2018/0353662 | A1* | 12/2018 | Locke | A61F 13/00068 |
| 2018/0353663 | A1* | 12/2018 | Locke | A61F 13/00063 |
| 2020/0268561 | A1* | 8/2020 | Locke | A61F 13/00068 |
| 2020/0337906 | A1* | 10/2020 | Long | A61L 15/58 |

FOREIGN PATENT DOCUMENTS

| | | | |
|---|---|---|---|
| AU | 755496 | B2 | 12/2002 |
| CA | 2005436 | A1 | 6/1990 |
| DE | 26 40 413 | A1 | 3/1978 |
| DE | 43 06 478 | A1 | 9/1994 |
| DE | 29 504 378 | U1 | 9/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | A1 | 7/2000 |
| GB | 692578 | A | 6/1953 |
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |
| WO | 2009146441 | A1 | 12/2009 |
| WO | 2014140578 | A1 | 9/2014 |
| WO | 2019027731 | A1 | 2/2019 |
| WO | 2019063488 | A2 | 4/2019 |
| WO | 2019067264 | A1 | 4/2019 |
| WO | 2020159677 | A1 | 8/2020 |

OTHER PUBLICATIONS

Susan Mendez-Eatmen, RN; "When wounds Won't Heal" RN Jan. 1998, vol. 61 (1); Medical Economics Company, Inc, Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (ertified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

(56) References Cited

OTHER PUBLICATIONS

D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C® Therapy Clinical Guidelines: A Reference Source for Clinicians; Jul. 2007.
International Search Report and Written Opinion for Corresponding Application No. PCT/US2020/030528 mailed Sep. 17, 2020.
European Examination Report for corresponding application 20728283.1, dated Sep. 6, 2024.
Extended European Search Report for corresponding application 26165970.0, dated Jun. 10, 2026.

* cited by examiner

ABDOMINAL NEGATIVE-PRESSURE THERAPY DRESSING WITH CLOSED-LOOP FORCE MANAGEMENT CONTROL

RELATED APPLICATIONS

The present application claims priority to U.S. Provisional Patent Application No. 62/862,417, entitled "Abdominal Negative-Pressure Therapy Dressing with Closed-Loop Force Management Control," filed Jun. 17, 2019, which is incorporated herein by reference for all purposes.

TECHNICAL FIELD

The invention set forth in the appended claims relates generally to tissue treatment systems and more particularly, but without limitation, to abdominal negative pressure therapy systems.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

BRIEF SUMMARY

New and useful systems, apparatuses, and methods for closed-loop force management control in a negative-pressure therapy environment are set forth in the appended claims. Illustrative embodiments are also provided to enable a person skilled in the art to make and use the claimed subject matter.

For example, in some embodiments, a system of control of the forces applied to an abdominal wound dressing or other open-wound dressing is described. Strain sensors (e.g., measure force, stress, or strain) are integrated within or applied to the top of the dressing. These sensors can provide data to a control system that allows the control system to modulate the closure forces by varying the applied pressure. The data may be monitored over time to provide feedback to the user about wound and physical factors, such as edema reduction or closure of a wound.

More generally, some embodiments of a dressing for treating an open abdominal cavity with negative pressure may comprise a first layer comprising a spacer manifold and a contact film enclosing the spacer manifold; a second layer comprising a closure manifold configured to be disposed adjacent to the contact film; and a sensor configured to acquire data associated with strain in one or more of the closure manifold and the spacer manifold. In some embodiments, the data may comprise changes in capacitance based on displacement of the sensor. In some embodiments, the sensor may comprise an electroactive polymer. Additionally or alternatively, the dressing may further comprise a wireless transmitter coupled to the sensor in some embodiments. In some embodiments, the sensor may be coupled to the closure manifold.

In other aspects, an apparatus for treating an open abdominal cavity with negative pressure may comprise a first layer comprising a spacer manifold and a contact film enclosing the spacer manifold; a second layer comprising a closure manifold configured to be disposed adjacent to the contact film; a sensor configured to acquire data associated with strain in one or more of the spacer manifold and the closure manifold; a negative-pressure source configured to be fluidly coupled to the closure manifold; and a controller configured to receive the data from the sensor and operate the negative-pressure source to generate negative pressure based on the data. The controller may be configured to operate the negative-pressure source to maintain a strain target based on the data. In some embodiments, the data may comprise changes in capacitance based on displacement of the sensor. In still further embodiments, the sensor may comprise an electroactive polymer. Additionally or alternatively, a wireless transmitter may be coupled to the sensor in some embodiments. In some embodiments, the sensor may be coupled to the closure manifold.

In some examples, an apparatus for treating an open abdominal cavity with negative pressure may comprise a first layer comprising a film configured to contact an organ in the abdominal cavity; a second layer comprising a distribution material configured to distribute a negative pressure, the second layer configured to be disposed adjacent to the first layer; and one or more detectors or sensors configured to take measurements of strain in one or more of the first layer and the second layer. A negative-pressure source may be configured to be fluidly coupled to the second layer, and a controller can be configured to receive the measurements from the one or more detectors and operate the negative-pressure source to generate negative pressure based on the measurements.

Examples of a dressing for treating an open abdominal cavity with negative pressure are also provided. In some embodiments, the dressing may comprise a first layer comprising a spacer manifold and a contact film enclosing the spacer manifold, the spacer manifold comprising a central manifold, a first extension coupled to the central manifold, and a second extension coupled to the central manifold; a second layer comprising a closure manifold configured to be disposed proximate to the central manifold; a first sensor configured to acquire data associated with strain in the first extension; a second sensor configured to acquire data associated with strain in the second extension; and a third sensor configured to acquire data associated with strain in the closure manifold.

A method for treating an open abdominal cavity with negative pressure is also described. In some embodiments, the method may comprise applying a first dressing layer over viscera; applying a second dressing layer over the first dressing layer in an abdominal opening; applying a cover over the second dressing layer; sealing the cover to epidermis around the abdominal opening; fluidly coupling a negative-pressure source to the second dressing layer through the cover; operating the negative-pressure source to deliver negative pressure to the second dressing layer; periodically measuring strain in one or more of the first dressing layer and the second dressing layer; and operating the negative-pressure source to increase the negative pressure if the strain decreases.

A dressing for treating an open abdominal cavity with negative pressure is described. In some embodiment, the dressing may comprise a viscera contact layer capable of communicating a negative pressure to the viscera and capable of forming flow paths for a fluid through the contact layer; a fluid manifold capable of being disposed adjacent to the contact layer and capable of communicating a negative pressure to a tissue and capable of forming flow paths for a fluid; and a sensor capable of acquiring data associated with strain in one or more of the fluid manifold and the viscera contact layer.

A dressing for treating an open abdominal cavity with negative pressure is described. In some embodiments, the dressing comprises: i) a first layer comprising a first fluid manifold capable of communicating a negative pressure to the abdominal cavity and capable of forming flow paths for a fluid, and a contact film enclosing the first fluid manifold, the first fluid manifold comprising a central portion and first and second extension portions coupled to the central portion; ii) a second layer comprising a second fluid manifold capable of communicating a negative pressure to the first layer, the second layer capable of being disposed proximate to the central portion of the first manifold; and iii) a first strain sensor capable of detecting strain in the first fluid manifold.

A method for treating an open abdominal cavity with negative pressure is disclosed. In some embodiments, the method comprising: i) applying a first dressing layer over viscera; ii) applying a second dressing layer over the first dressing layer in an abdominal opening; iii) applying a cover over the second dressing layer; iv) sealing the cover to epidermis around the abdominal opening; v) fluidly coupling a negative-pressure source to the second dressing layer through the cover; vi) operating the negative-pressure source to deliver negative pressure to the second dressing layer; and vii) periodically measuring strain in one or more of the first dressing layer and the second dressing layer.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
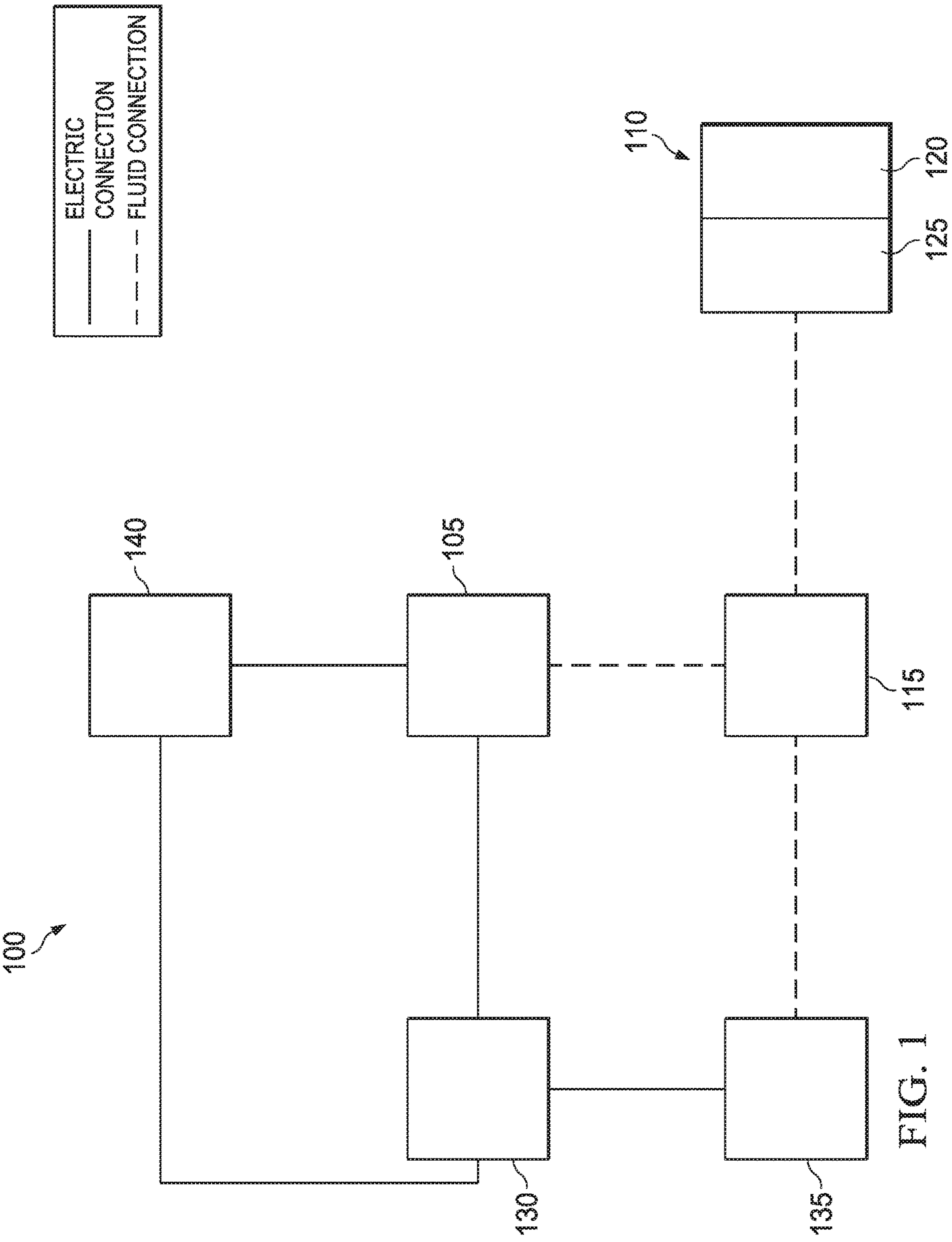
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumen or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130 and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between about −5 mm Hg (−667 Pa) and −500 mm Hg (−66.7 kPa). Common therapeutic ranges are between about −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or a computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezoresistive strain gauge. In some embodiments, the strain gauge may be fluidly coupled to the dressing 110 or may be in the dressing 110. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal. In some examples, the signal may be transmitted wirelessly.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. For example, the tensile strength of foam may be increased for instillation of topical treatment solutions. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface 120 may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. A hydrophobic material can be any material having a solubility in water of less than 10 mg/L at standard temperature and pressure. A hydrophilic material can be any material having a solubility in water of 10 mg/L and greater at standard temperature and pressure. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inspire 2327 polyurethane films, commercially available from Expopack Advanced Coatings, Wrexham, United Kingdom. In some embodiments, the cover 125 may comprise INSPIRE 2301 having an MVTR (upright cup technique) of 2600 $g/m^2/24$ hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, or silicone gel.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115. As used in this disclosure and in the claims below, the term "strain" may be used to refer to any deformation, such as twisting, bending, pressure, compression, stretching, or the like. The term "strain" may include a force on a sensor that causes or may cause deformation. The term "strain" may be a change in length of a physical dimension of the sensor with respect to a reference length of that physical dimension. The reference length of a material may be the length of the dimension before a sensor is incorporated into the dressing, the length of the dimension after being applied to the dressing, the length of the dimension at the time the dressing is first placed under a target negative pressure in a NPWT, or what the target length of the material in the dressing will be when the wound is healed.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Figure 2:
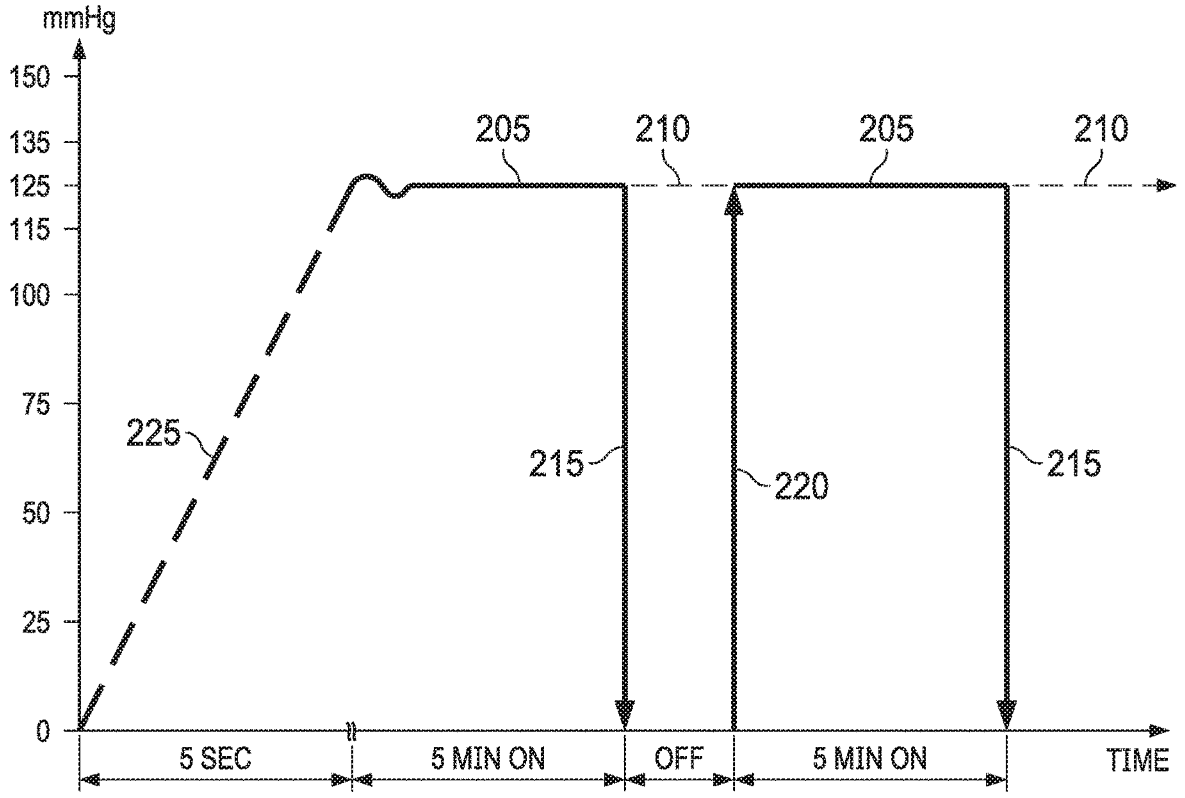
FIG. 2 is a graph illustrating additional details of example pressure control modes that may be associated with some embodiments of the therapy system of FIG. 1.

FIG. 2 is a graph illustrating additional details of an example control mode that may be associated with some embodiments of the controller 130. In some embodiments, the controller 130 may have a continuous pressure mode, in which the negative-pressure source 105 is operated to provide a constant target negative pressure, as indicated by line 205 and line 210, for the duration of treatment or until manually deactivated. Additionally or alternatively, the controller may have an intermittent pressure mode, as illustrated in the example of FIG. 2. In FIG. 2, the x-axis represents time and the y-axis represents negative pressure generated by the negative-pressure source 105 over time. In the example of FIG. 2, the controller 130 can operate the negative-pressure source 105 to cycle between a target pressure and atmospheric pressure. For example, the target pressure may be set at a value of 135 mmHg, as indicated by line 205, for a specified period of time (e.g., 5 min), followed by a specified period of time (e.g., 2 min) of deactivation, as indicated by the gap between the solid lines 215 and 220. The cycle can be repeated by activating the negative-pressure source 105, as indicated by line 220, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time, as indicated by the dashed line 225. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time, as indicated by the solid line 220, may be a value substantially equal to the initial rise time as indicated by the dashed line 225.

Figure 3:
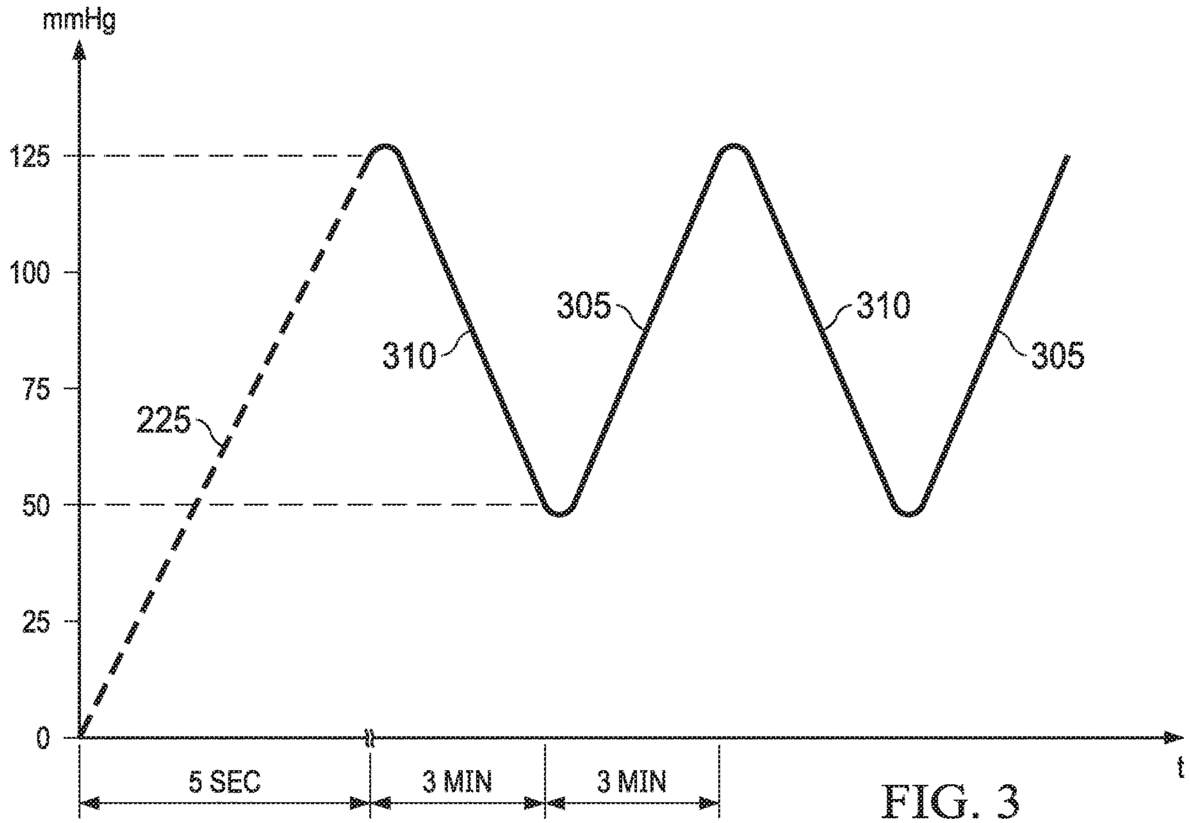
FIG. 3 is a graph illustrating additional details that may be associated with another example pressure control mode in some embodiments of the therapy system of FIG. 1.

FIG. 3 is a graph illustrating additional details that may be associated with another example pressure control mode in some embodiments of the therapy system 100. In FIG. 3, the x-axis represents time and the y-axis represents negative pressure generated by the negative-pressure source 105. The target pressure in the example of FIG. 3 can vary with time in a dynamic pressure mode. For example, the target pressure may vary in the form of a triangular waveform, varying between a negative pressure of 50 and 135 mmHg with a rise time 305 set at a rate of +25 mmHg/min. and a descent time 310 set at −25 mmHg/min. In other embodiments of the therapy system 100, the triangular waveform may vary between negative pressure of 25 and 135 mmHg with a rise time 305 set at a rate of +30 mmHg/min and a descent time 310 set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 4:
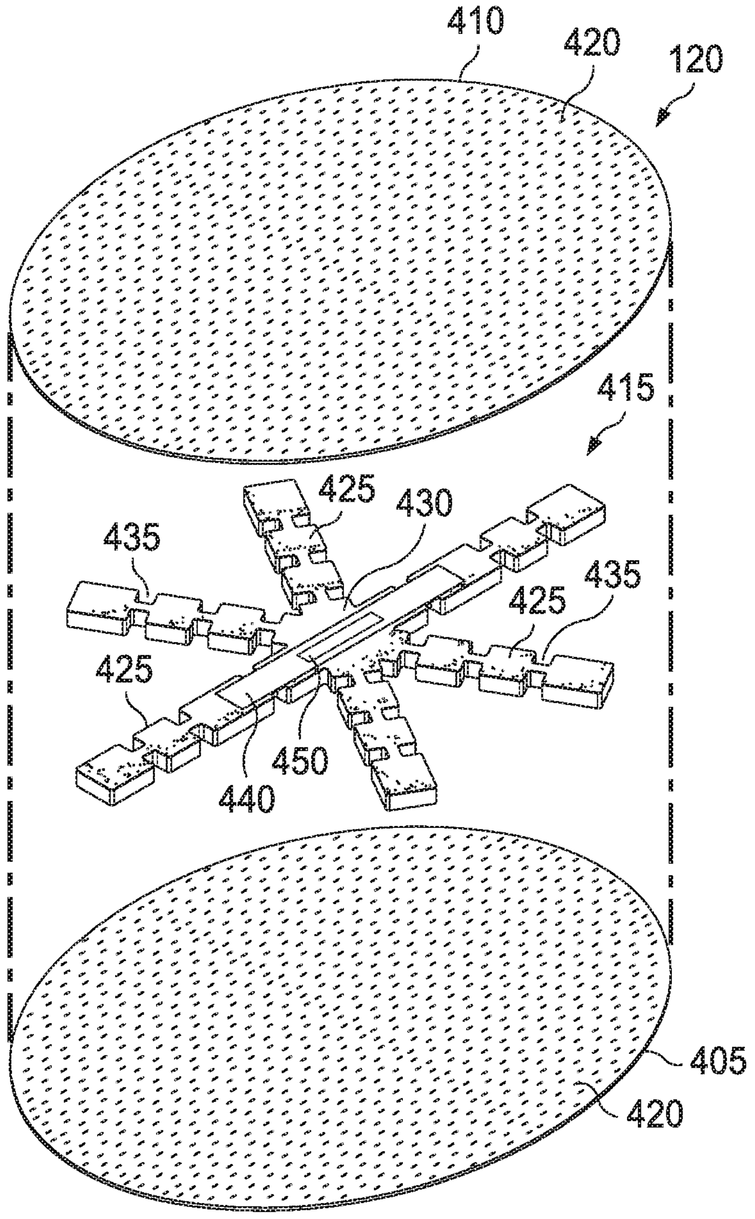
FIG. 4 is an assembly diagram illustrating additional details that may be associated with an exemplary tissue interface of the dressing in FIG. 1.

FIG. 4 is an assembly diagram of an example of the tissue interface 120, illustrating additional details that may be associated with some example embodiments having multiple layers. In the example embodiment of FIG. 4, the tissue interface 120 generally includes a first contact layer 405, a second contact layer 410, and a spacer layer 415. Each of the first contact layer 405, the second contact layer 410, and the spacer layer 415 may be a manifold. For example, as illustrated in FIG. 4, the first contact layer 405 and the second contact layer 410 may have fenestrations 420 suitable for distributing or collecting fluid across the tissue interface 120. The fenestrations 420 can have a variety of suitable shapes. For example, the fenestrations 420 may be circular or rectangular. In FIG. 4, the fenestrations 420 are slits. In some examples, the spacer layer 415 may be formed from a porous material, such as open-cell foam.

The first contact layer 405, the second contact layer 410, and the spacer layer 415 may also be sufficiently flexible to conform to a tissue site. For example, the first contact layer 405 and the second contact layer 410 may be a thin polymer film or sheet of construction similar to the cover 125. A thickness of about 50 microns to about 120 microns may be suitable for some embodiments of the first contact layer 405 and the second contact layer 410. The spacer layer 415 may be a flexible foam in some examples. The profile of the spacer layer 415 may also provide flexibility. In some examples, the spacer layer 415 may have a profile that is coextensive with the first contact layer 405, the second contact layer 410, or both. In the example of FIG. 4, the spacer layer 415 has a star profile having a plurality of appendages, such as spacer legs 425, coupled to and radiating from a central body 430. The spacer legs 425 in such a configuration can be manipulated to conform to various types of tissues sites having complex geometries. Other suitable profiles may include interconnected concentric rings or arcs, or some combination of appendages, rings, and arcs, which may be coupled to or form a central body. In some examples, the spacer legs 425 or other appendages may comprise a plurality of joints 435, which can further increase flexibility.

The tissue interface 120 may additionally comprise at least one strain sensor 440 and at least one transmitter 450 coupled to the strain sensor 440. In the embodiment in FIG. 4, the strain sensor 440 and the transmitter 450 are disposed within or on the surface of the spacer layer 415 and within the space formed by first contact layer 405 and the second contact layer 410.

The transmitter 450 of FIG. 4 may be placed within the tissue interface 120 and particularly on or within the spacer layer 415, which can be optimized to provide optimal closure forces for the abdominal wall and the fascia. In alternate embodiments, the strain sensor 440 and the transmitter 450 may be affixed to the external or internal surfaces of the first contact layer 405 or the second contact layer 410 to record the force on one or more axes over the tissue interface 120. By way of example and not limitation, the strain sensor 440 and the transmitter 450 may be integrated in one or more of the spacer legs 425. Alternatively, the strain sensor 440 may be stretched between two of the spacer legs 425 and across the central body 430 of spacer layer 415, as shown in FIG. 4. In some embodiments, the strain sensor 440 can acquire data associated with strain across the central body 430. In other embodiments, the strain sensor 440 can acquire data associated with strain across a square perimeter surrounding the central body 430. In still other embodiments, the strain sensor 440 can acquire data associated with strain along one or more axes of the central body 430.

Many types of strain sensors may be suitable for use with the therapy system 100. The strain sensor may be a capacitor, including a stretchable capacitor. The stretchable capacitor may contain a non-stretchable dielectric material positioned between two stretchable electrodes, may contain a stretchable dielectric material positioned between two non-stretchable electrodes, and/or may contain a stretchable dielectric material positioned between two stretchable electrodes. Electroactive polymer (EAP) sensors may be particularly advantageous for some embodiments. An EAP is a polymer that undergoes a change in size or shape upon the application of an electric field. The EAP sensors can work via measurement of the change in capacitance. For example, the change in capacitance of an EAP sensor may be due to a change in physical deformation (i.e., a displacement-to-capacitance transducer). EAP sensors are typically constructed from a dielectric polymer film that is positioned between two stretchable electrodes. As the dielectric film is stretched or strained, the film thins or expands within the area and subsequently increases or decreases in capacitance. Non-limiting examples of such sensors are manufactured by Parker Hannafin Corporation. EAP sensor are flexible and can provide graduated feedback.

Figure 5:
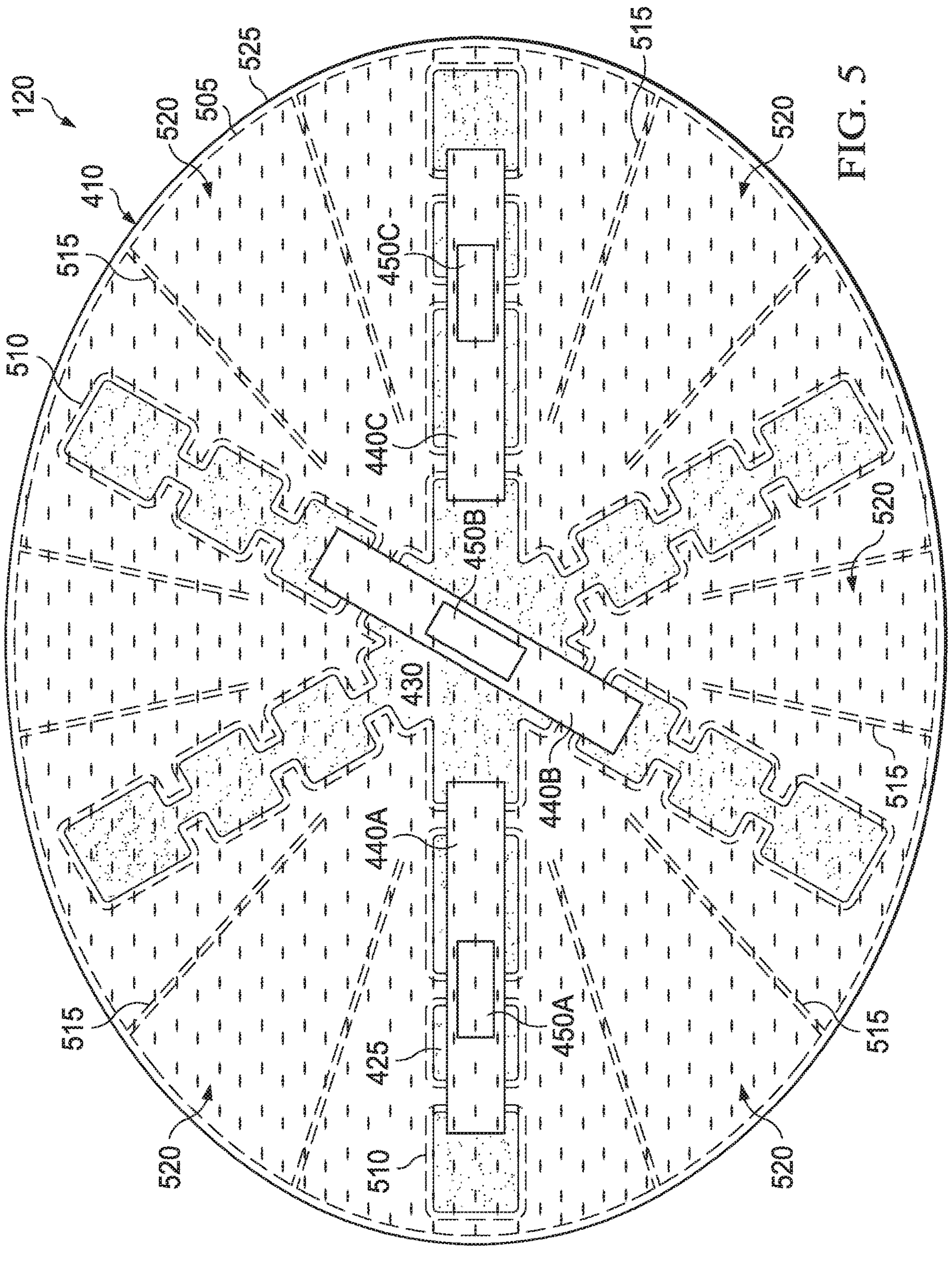
FIG. 5 is a top view illustrating still more details that may be associated with the exemplary tissue interface of the dressing in FIG. 1.

FIG. 5 is a top view of the tissue interface 120 of FIG. 4, as assembled, illustrating additional details that may be associated with some examples. As illustrated in the example of FIG. 5, the first contact layer 405 (not visible) and the second contact layer 410 can be geometrically similar and/or may be congruent in some embodiments. A plurality of bonds may be used to couple the first contact layer 405 to the second contact layer 410. The bonds may be formed using any known technique, including without limitation, welding (e.g., ultrasonic or RF welding), bonding, adhesives, cements, or other bonding technique or apparatus. In the example of FIG. 5, the bonds include peripheral bonds 505, spacer bonds 510, and directional bonds 515.

In the exemplary embodiment in FIG. 5, a plurality of strain detectors or sensors and transmitters are configured to measure strain in tissue interface 120. For example, in FIG. 5 a first strain sensor 440A and a first transmitter 450A are disposed on a first spacer leg 425 of the spacer layer 415. A second strain sensor 440B and a second transmitter 450B are disposed on a second spacer leg and a third spacer leg of the spacer layer 415, across the central body 430 of the spacer layer 415. A third strain sensor 440C and a third transmitter 450C are disposed on a fourth spacer leg of the spacer layer 415. In alternate embodiments, there may be more than three strain sensors 440 and transmitters 450 or less than three strain sensors 440 and transmitters 450. Additionally, the strain sensors 440 and transmitters 450 need not be attached to the spacer layer 415. By way of example, the strain sensors 440 and the transmitters 450 may be attached to an inner surface or an outer surface of the first contact layer 405 (not visible) or to an inner surface or an outer surface of the second contact layer 410. In some embodiments, the first contact layer 405, the second contact layer 410, or both may comprise a central area and a periphery, and one or more of the strain sensors may be configured to acquiring data associated with strain in a direction radial from and/or in the central area.

The peripheral bonds 505 may be disposed around a periphery of the first contact layer 405 and the second contact layer 410, which can bond the first contact layer 405 to the second contact layer 410. The spacer bonds 510 can be disposed around the spacer layer 415, which can secure the spacer layer 415 in a fixed position relative to the first contact layer 405 and the second contact layer 410. In some embodiments, the directional bonds 515 can define one or more flow paths 520 toward the central body 430. For example, the directional bonds 515 are disposed between the spacer legs 425, and generally extend radially between the central body 430 and the peripheral bonds 505.

The strain sensors 440 and the transmitters 450 can be configured to monitor and measure force applied by the removal of air from the dressing 110 at any pressure and to transmit the measured data to the controller 130. The measured force can be correlated to a resistive force of a patient's tissues. The data may be used to control the negative pressure to maintain a constant lateral strain over time or to achieve a specific desired strain profile.

For example, the strain delivered by the tissue interface 120 at a set pressure may drop over time as the tissue margins re-approximate and edema is reduced. The strain sensors can detect the change in strain and the controller 130 can increase the negative pressure to increase the strain back to an optimum level for the duration of treatment. If the wound closes to a degree that the density of the foam at any pressure does not allow the dressing strain to be increased, the controller 130 may report this condition to the operator. The operator may then perform a dressing change to a smaller piece of foam or a less dense wound filler. This would allow the controller 130 to continue to deliver optimum or profiled strain as selected by the operator.

As another example, the strain delivered by the tissue interface 120 at a set pressure may increase due to increased edema or increased opening of the wound. The strain sensors may detect the change in strain and the controller 130 may increase the negative pressure to reduce the edema or opening in the wound, which will decrease the strain measured by the sensor back to an optimum level for the duration of treatment. If the strain continues to increase at a set pressure, the controller 130 may report this condition to the operator. The operator may then perform additional treatments to reduce the edema or to increase closure of the wound. This would also allow the controller 130 to continue to deliver optimum or profiled strain as selected by the operator.

Figure 6:
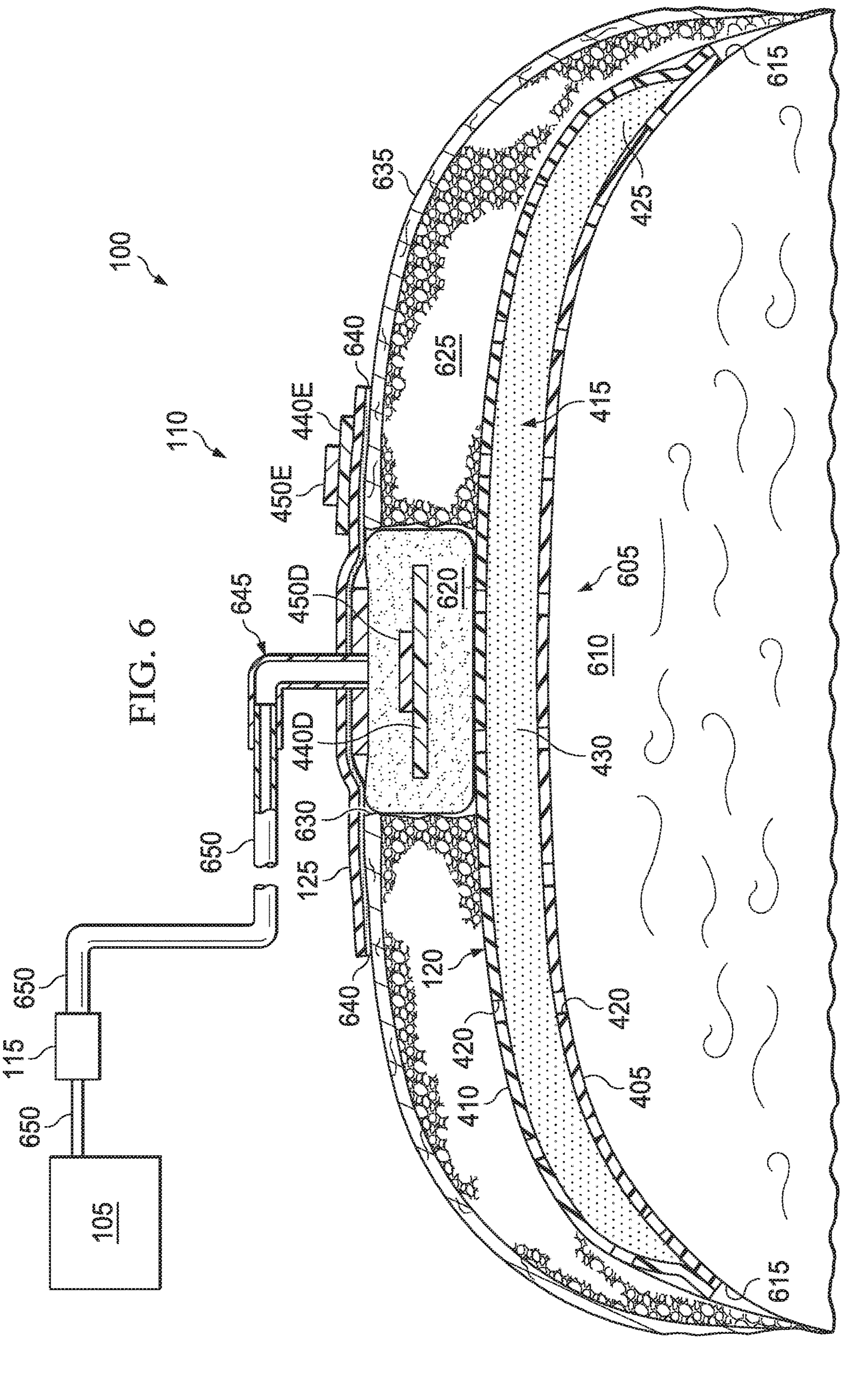
FIG. 6 is a schematic view of an exemplary tissue interface applied to a tissue site that comprises an abdominal cavity.

FIG. 6 is a schematic view of an example of the tissue interface 120 applied to a tissue site that comprises an abdominal cavity 605. The tissue interface 120 is flexible and can be inserted into the abdominal cavity 605. In the example of FIG. 6, the tissue interface 120 is applied over viscera and supported by abdominal contents 610. For example, the first contact layer 405 may be configured to contact an organ in the abdominal cavity 605. A portion of the tissue interface 120, such as one or more of the spacer legs 425, may be disposed in or proximate to the paracolic gutter 615. While the exemplary embodiment in FIG. 6 is applied to the abdomen, it will be appreciated that the tissue interface 120 and the associated technique can be applied to other open wounds where closure of swollen and traumatized tissues by re-approximation are desired.

In the example of FIG. 6, the first contact layer 405 and the second contact layer 410 are coupled to form a viscera contact layer. In some embodiments, the viscera contact layer can be configured to communicate negative pressure to the viscera. For example, flow paths may be formed between the first contact layer 405 and the second contact layer 410. Additionally, or alternatively, the viscera contact layer can enclose the spacer manifold 415 as illustrated in the example of FIG. 6. The dressing 110 of FIG. 6 includes a closure manifold 620, which can be fluidly coupled to the tissue interface 120 and be configured to deliver negative pressure through the abdominal wall 625. For example, the closure manifold 620 may be inserted through an opening 630 in the abdominal wall 625 and disposed adjacent to the tissue interface 120 in fluid communication with at least some of the fenestrations 420 in the second contact layer 410. The cover 125 may be placed over the opening 630 and sealed to epidermis 635 around the opening 630. For example, an attachment device such as an adhesive layer 640 may be disposed around a perimeter of the cover 125 to secure the cover 125 to the epidermis 635.

Additionally, FIG. 6 includes a strain sensor 440D that is disposed within the closure manifold 620, and a transmitter 450D that is mounted on and coupled to the strain sensor 440D. The strain sensor 440D and the transmitter 450D are configured to monitor and measure the force applied to the closure manifold 620 and to transmit the measured data to the controller 130. This enables the resistive force of abdominal wall 625 on closure manifold 620 and opening 630 to be monitored.

In some embodiments, one or more sensors may additionally or alternatively be mounted on an edge of the cover 125. For example, FIG. 6 further includes a strain sensor 440E that is mounted on the surface of cover 125, where the surface of the cover 125 is in direct contact with the epidermis 635. A transmitter 450E may be mounted on and coupled to the strain sensor 440E. The strain sensor 440E and the transmitter 450E are configured to monitor and measure the force applied to the cover 125 and to transmit the measured data to the controller 130. Since the cover 125 is adhered to the epidermis 635 around the opening 630, this enables the resistive force of the epidermis 635 on cover 125 to be monitored.

FIG. 6 further illustrates an example of a dressing interface 645 fluidly coupling the dressing 110 to a fluid conductor 650. The dressing interface 645 may be, as one example, a port or connector, which permits the passage of fluid from the closure manifold 620 to the fluid conductor 650 and vice versa. The dressing interface 645 of FIG. 6 comprises an elbow connector. Fluid collected from the abdominal cavity 605 may enter the fluid conductor 650 via the dressing interface 645. In other examples, the therapy system 100 may omit the dressing interface 645, and the fluid conductor 650 may be inserted directly through the cover 125 and into the closure manifold 620. In some examples, the fluid conductor 650 may have more than one lumen. For example, the fluid conductor 650 may have one lumen for negative pressure and liquid transport, one or more lumens for communicating pressure to a pressure sensor, and one or more lumens for delivering installation fluid to the wound.

A negative pressure may be applied to the central body 430 or elsewhere to cause fluid flow through the fenestrations 420. The fenestrations 420 can allow fluid to be collected or distributed through and across the first contact layer 405 and the second contact layer 410 under negative pressure. Fluid can move directly or indirectly towards the negative-pressure source 105 through the fenestrations 420. In some examples, additional features such as the directional bonds 515 may direct flow toward the central body 430. For example, fluid can move through the spacer layer 415, through micro-channels formed between the first contact layer 405 and the second contact layer 410, or both. Negative pressure may be distributed more directly through the spacer layer 415, and can be the dominant pathway. In some examples, the spacer layer 415 may be omitted or replaced with an absorbent layer and fluid can move through the absorbent layer and/or micro-channels formed between the first contact layer 405 and the second contact layer 410.

Figure 7:
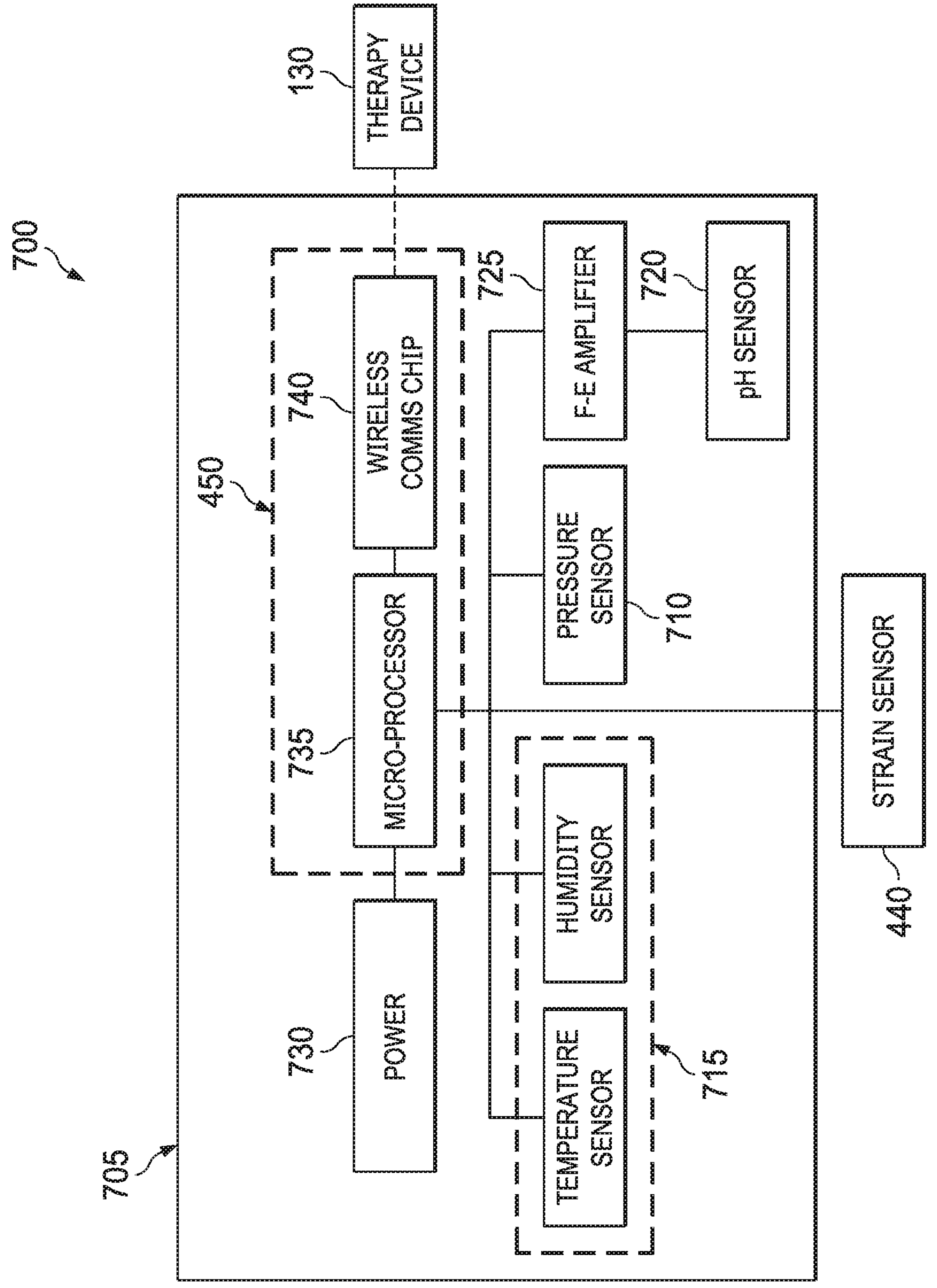
FIG. 7 is a schematic diagram of the wireless capable sensors associated with the exemplary tissue interfaces.

FIG. 7 is a schematic diagram of an example of a sensor module 700 that may be associated with some embodiments of the therapy system 100. In some examples, the transmitter 450 may be coupled to or integrated with the sensor module 700, as illustrated in the sensor module 700 of FIG. 7. The sensor module 700 may comprise a housing 705 that contains a circuit board (not shown) on which may be mounted a pressure sensor 710, a humidity sensor 715, a pH sensor 720, a front-end amplifier 725, and a power source 730. The sensor module 700 may additionally comprise a temperature sensor that can be a component of either the pressure sensor 710 or the humidity sensor 715. The transmitter 450 is configured to be attached, and electrically coupled, to the strain sensor 440.

The transmitter 450 is capable of two-way wireless communication and/or wired communication with the controller 130, which may be, for example, integral with therapy unit, a tablet computer, a desktop computer, or another similar device. The transmitter 450 may further comprise a controller 735 (e.g., a microprocessor) and a wireless communication chip 740 that communicates with the controller 130 under control of the controller 735. The housing 705 provides a moisture-proof enclosure for the internal circuit board and the components mounted thereon. Controller 130 may process the measured pressure, humidity, pH, and strain to assist in performing therapy using a closed-loop algorithm. Additionally or alternatively, at least some of the sensors may provide information about the condition of the skin and underlying tissue. For example, the strain sensor 440 can further measure pH and temperature, which can indicate infection if pH is alkaline and temperature is elevated. Moisture sensing of the tissue by an electro-conductive system or through exposure of a humidity sensor to epidermis may be an indicator of edema, and can be measured over time to determine if the level of moisture is decreasing with therapy as expected.

Using a transmitter 450 that is wireless has the advantage of eliminating an electrical conductor between the transmitter 450 and the controller 130, which may become entangled with the fluid conductor 650 when in use during therapy treatments. The wireless communication chip 740 may comprise an integrated device that implements Bluetooth® Low Energy wireless technology. In some examples, the transmitter 450 may be a Bluetooth® Low Energy system-on-chip that includes a microprocessor, such as the nRF51822 chip available from Nordic Semiconductor. The transmitter 450 may be implemented with other wireless technologies suitable for use in the medical environment.

In some embodiments, the power source 730 may be, for example, a battery that may be a coin cell battery having a low-profile that provides a 3-volt source for the transmitter 450 and other electronic components within the sensor module 700. In some embodiments, the power source 730 is a power source located outside of housing 705. In some example embodiments, all of the components within housing 705 associated with the sensor module 700 may be integrated into a single package.

Each of the component sensors of sensor module 700 may comprise a sensing portion (or probe) that extends outside of housing 705 in order to make contact with fluids from the wound so that temperature, pressure and pH may be measured. The front-end amplifier 725 may amplify the measured pH value detected by pH sensor 720.

In some embodiments, the pressure sensor 710 may be a piezoresistive pressure sensor having a pressure-sensing element covered by a dielectric gel such as, for example, a Model 1620 pressure sensor available from TE Connectivity. The dielectric gel provides electrical and fluid isolation from the bodily fluids in order to protect the sensing element from corrosion or other degradation.

In some examples, the pressure sensor 710 may comprise a temperature sensor for measuring the temperature of the fluids from the wound. In other embodiments, the humidity sensor 715 may comprise a temperature sensor for measuring the temperature. In some embodiments, the humidity sensor 715 may also comprise a temperature sensor may be a single integrated device such as, for example, Model HTU28 humidity sensor also available from TE Connectivity.

In some examples, the controller 735 may be configured to detect changes in the capacitance of the strain sensor 440 as the physical force (or strain) on strain sensor 440 changes with increases or decreases in the force exerted by the bodily tissues or exerted by the negative pressure. In some embodiments, the transmitter 450 may be integrated within the dressing 110, and power may be provided by an integrated battery with sufficient power to last for at least 7 days. For the re-usable external approach, the operational power can be provided by an internal cell, which can be re-charged by either a wired connection or via wireless charging. In some examples, the secondary coil is integrated within the module or within the top layer of the dressing 110.

In some embodiments, the tissue interface 120, closure manifold 620, and/or cover 125 may be supplied with affixed mounting points for the strain sensor 440 and the transmitter 450. The mounting points can be a mechanical latch point. In some embodiments, there can be mechanical latch points for the transmitter 450 and a further latch point for the end of the strain sensor 440, such that the strain sensor 440 stretches over the collapse area of a tissue site. Alternatively, adhesive regions may be provided on the tissue interface 120, closure manifold 620, and/or cover 125, which can be exposed by removing or peeling of a liner to allow the strain sensor 440 and/or the transmitter 450 to be attached. In some examples, the adhesive regions may comprise or consist essentially of light-switchable adhesives. The light-switchable adhesives can be switched to deactivate or activate the adhesive by exposure to visible or ultra violet light. In some instances, the light deactivates the adhesive when the strain sensor 440 is to be removed. The adhesive can be exposed to light either by a light-blocking layer which is exposed to ambient light or by the use of an ultraviolet light source. Such mechanical latching and adhesive options will be known to one with skilled in the art and are not specifically described here, but may be twist latched, snap-fits or other types.

The strain sensor 440 can be used to measure and record the strain dynamically, so that the negative pressure may be closed-loop controlled using strain measurements instead of negative pressure measurements. For example, the controller 130 can be configured to operate the negative-pressure source 105 to maintain a strain target based on data from the strain sensor 440. The pressure delivered may be varied to achieve the desired strain and closure force level. This may also be used to provide periodic closed-loop control of intermittent stress and relaxation cycles to stimulate cell division. One or more of the strain sensors 440 may be incorporated within and along the dressing length. If the strain sensors 440 are in a fluid pathway, they may be perforated to allow fluid flow through the strain sensor 440.

In some embodiments, the strain sensor 440 may be extended to approximately 150% of its length, thereby providing a high strain reading within the measurement system. As a tissue site is drawn down, the collapse of the dressing can reduce the measurement of the strain on the strain sensor 440 due to the reduction in its length. The strain force may reach steady state within approximately 30 minutes. At this time, further closure of the tissue site may result in a continuing rate of reduction in measured strain over time. If the tissue site stops closing or becomes edematous, the strain measurement becomes static or may increase if the tissue site begins to re-open or swell. The controller 130 can be configured to operate the negative-pressure source 105 to maintain a constant rate of change on the strain sensor 440. The constant rate of change can mimic a reduction in stretch deformation and strain on the strain sensor 440 that corresponds to constant closure and re-approximation of the tissue site.

Figure 8:
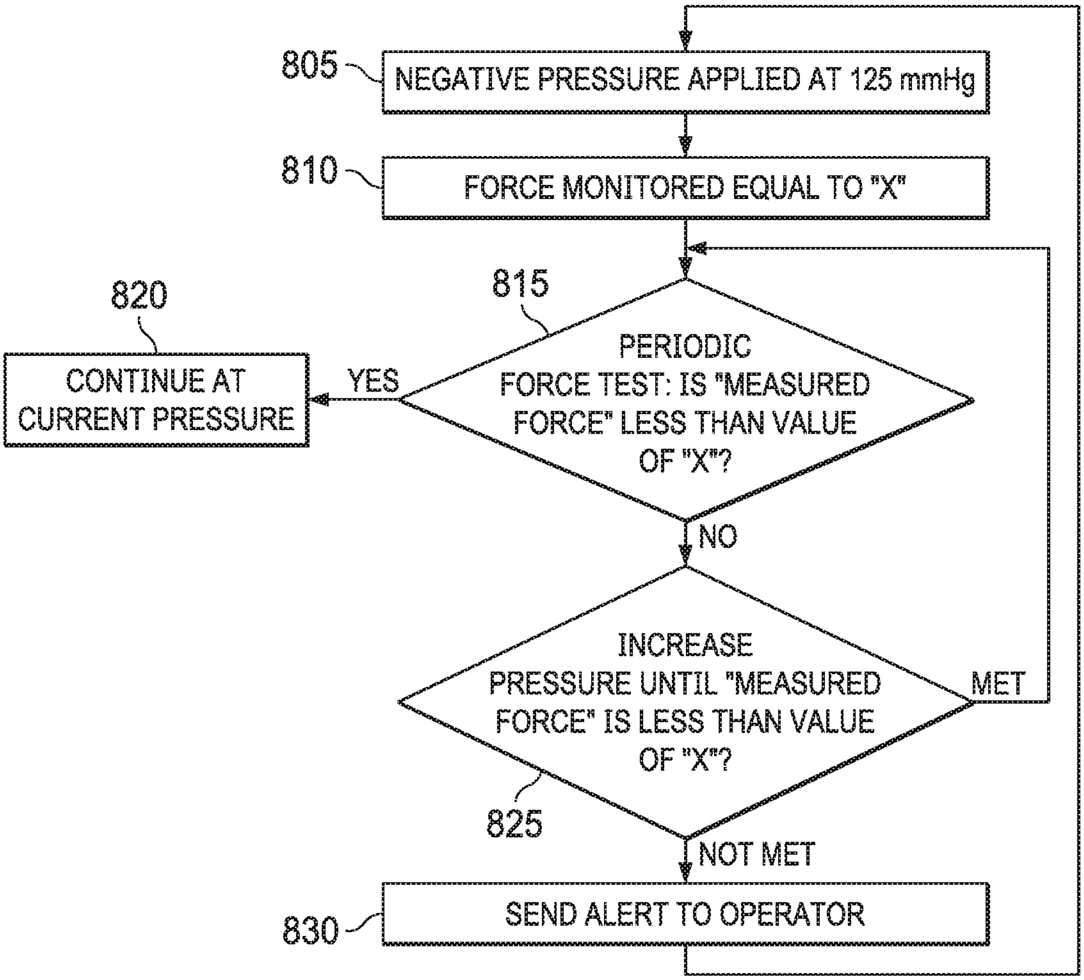
FIG. 8 is a flow diagram illustrating the operation of the wireless capable sensors in FIG. 7.

FIG. 8 is a flow diagram illustrating example operations that may be associated with some embodiments of the therapy system 100. Initially, in 805, negative pressure may be applied at an exemplary pressure of 125 mmHg. In 810, transmitter 450 monitors force (from strain sensor 440) and measures a force equal to a value "X". In some embodiments, a measurement of force equal to a value of "X" is a preset value or a value set by an operator of the therapy system. The value of "X" may also vary over time, such as to follow a schedule or program. The measure value of X is reported to the controller 130. Thereafter, in 815, transmitter 450 periodically performs a force test to verify that the "Measured Force" is less than value of "X". If the newly measured force is less than the value X, then, in 820, the controller 130 continues to operate at the current negative pressure.

However, if the newly measured force is not less than the value X, then, in 825, the controller 130 increases the negative pressure until the Measured Force is less than value X. If the controller 130 is able to reduce the Measured Force to less than the value X, then the transmitter 450 continues to perform the periodic force test in 815. If the controller 130 is not able to reduce the Measured Force to less than the value X, then the controller 130 will send an alert message to the operator.

Advantageously, the use of a wireless transmitter 450 provides a capability of determining the location of the strain sensor 440 to ensure the strain sensor 440 is properly placed under the skin. Any external device capable of detecting the electromagnetic fields generated by the transmitter 450 is suitable for this purpose. In other embodiments, the strain sensor 440 or the wireless transmitter 450 may include an RFID tag that can be located by an RFID reader. Additionally, the strain sensor 440 or the wireless transmitter may be made from ultrasound opaque materials, X-ray opaque materials, or metals that can be easily detected by ultrasound scanners, X-ray scanners, or metal detectors, respectively.

The systems, apparatuses, and methods described herein may provide significant advantages. For example, dressing responses to negative pressure can cause closure forces that vary both temporally and spatially, and the therapy system 100 can acquire data corresponding to these closure forces. Some embodiments of the therapy system 100 can dynamically adjust and control the pressure at a tissue site based on these variations in order to maintain an optimal level of force on the dressing 110, to manage edema reduction, and to reverse expansion of the tissue site. Closure force data can also be monitored to provide feedback about tissue closure and physical factors such as edema. Wireless communications with sensors may be advantageous for some configurations. For example, closure forces may change slowly, which can reduce power requirements since the need for data bursts from sensors may be infrequent.

These principles may be applied to many types of tissue sites, including open wounds where closure is possible through re-approximation of the tissues, and other cases of compartment syndrome.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the sensor 130, the container 115, or any combination thereof may be separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating an open abdominal cavity with negative pressure, the dressing comprising:

a viscera contact layer configured to communicate a negative pressure to viscera and configured to form flow paths for a fluid through the viscera contact layer;

a spacer manifold enclosed by the viscera contact layer, the spacer manifold including a plurality of spacer legs extending from a central body;

a fluid manifold configured to be disposed adjacent to the viscera contact layer and configured to communicate the negative pressure to a tissue and capable of forming flow paths for the fluid; and at least one sensor including a stretchable material and being configured to acquire data associated with strain in one or more of the fluid manifold and the viscera contact layer, a first sensor of the at least one sensor disposed on a first leg of the plurality of spacer legs along a first axis, a second sensor of the at least one sensor disposed on a second leg of the plurality of spacer legs along a second axis, and a third sensor of the at least one sensor extending between two of the spacer legs and across the central body along a third axis, wherein at least one of the first axis and the second axis are different from the third axis, and wherein at least one of the first sensor, the second sensor, and the third sensor include an original length that is extended to a stretched length when the at least one sensor is disposed along the first axis, the second axis, or the third axis prior to treatment.

2. The dressing of claim 1, wherein the data comprises changes in capacitance based on deformation of the at least one sensor.

3. The dressing of claim 1, wherein the at least one sensor comprises a polymer that changes in size and/or in shape in the presence of an electric field.

4. The dressing of claim 1, wherein the at least one sensor comprises a stretchable capacitor.

5. The dressing of claim 1, further comprising a wireless transmitter coupled to the at least one sensor.

6. The dressing of claim 1, further comprising another of the at least one sensor coupled to the fluid manifold.

7. The dressing of claim 1, wherein the spacer manifold is configured to communicate the negative pressure to the tissue and configured to form flow paths for the fluid.

8. The dressing of claim 7, wherein the spacer manifold comprises open-cell foam.

9. The dressing of claim 1, wherein the fluid manifold comprises open-cell foam.

10. The dressing of claim 1, wherein the viscera contact layer comprises a polymer sheet forming openings configured to allow fluid to pass through the viscera contact layer, and wherein the fluid manifold is configured to fluidly communicate with the tissue and the spacer manifold through at least some of the openings in the viscera contact layer.

11. The dressing of claim 1, wherein the viscera contact layer comprises a periphery and a central area, and the at least one sensor is configured to acquire data associated with strain along one or more axes of the central area.

12. The dressing of claim 1, wherein a location of the at least one sensor is capable of being detected when the dressing is delivering negative pressure to the abdominal cavity.

13. The dressing of claim 1, wherein a location of the at least one sensor is capable of being detected by using one or more of electromagnetic fields, radio frequency, ultrasound, x-rays, and a magnetic field.

14. The dressing of claim 1, wherein the first sensor is stretched along the first axis to the stretched length, the second sensor is stretched along the second axis to the stretched length, and the third sensor is stretched along the third axis to the stretched length, and wherein the stretched length is up to 150 percent of the original length.

15. The dressing of claim 1, wherein the third sensor is stretched across the central body.

16. The dressing of claim 1, wherein the first sensor, the second sensor, and the third sensor are each associated with a physically and electronically separate circuit.

* * * * *